United States Patent [19]
Schlosser et al.

[11] Patent Number: 5,629,428
[45] Date of Patent: May 13, 1997

[54] 3-CHLOROPYRIDINES, AND THEIR USE IN LIQUID-CRYSTAL MIXTURES

[75] Inventors: Hubert Schlosser, Glashütten; Dietmar Jungbauer, Weiterstadt; Javier Manero, Frankfurt am Main, all of Germany

[73] Assignee: Hoechst Aktiengesellschaft, Frankfurt, Germany

[21] Appl. No.: 240,240

[22] Filed: May 10, 1994

[30] Foreign Application Priority Data

May 12, 1993 [DE] Germany ............... 43 15 867.6

[51] Int. Cl.$^6$ ............... C07F 5/02; C07F 7/04; C07D 405/12; C07D 403/10
[52] U.S. Cl. ............... 546/303; 546/13; 546/14; 546/281.7; 546/283.4; 546/283.7; 546/345; 544/333; 544/360; 349/182
[58] Field of Search ............... 546/303, 13, 14, 546/281.7, 283.7, 283.4; 544/333

[56] References Cited

U.S. PATENT DOCUMENTS

| | | | |
|---|---|---|---|
| 4,765,924 | 8/1988 | Inoue et al. | 252/299.61 |
| 4,898,455 | 2/1990 | Buchecker et al. | 350/350 R |
| 5,284,956 | 2/1994 | Buchecker et al. | 546/339 |

FOREIGN PATENT DOCUMENTS

| | | |
|---|---|---|
| 3701629 | 7/1987 | European Pat. Off. |
| 0228303 | 7/1987 | European Pat. Off. |
| 0239403 | 9/1987 | European Pat. Off. |
| 0242716 | 10/1987 | European Pat. Off. |
| 0361157 | 4/1990 | European Pat. Off. |
| 0391203 | 10/1990 | European Pat. Off. |
| 0573878 | 12/1993 | European Pat. Off. |
| 3702876 | 8/1988 | Germany . |
| 4026233 | 2/1991 | Germany . |
| 86/06373 | 11/1986 | WIPO . |
| WO91/04248 | 4/1991 | WIPO . |
| WO91/04249 | 4/1991 | WIPO . |
| WO92/11241 | 7/1992 | WIPO . |

OTHER PUBLICATIONS

L. A. Karamysheva et al., 1981, pp. 241–251, "New Heterocyclic Liquid Crystalline Compounds".

Liquid Crystals by Burrow et al., 1988, vol. 3, No. 12, pp. 1663–1653, "The Synthessis and Liquid Crystal Properties of some 2,5-disubstituted pyridines".

T. Geelhaar, 1st International Symposium on Ferroelectric Liquid Crystals, Arcachon, 12—23 Sep. 1987.

A. I. Pavlyuchenko, et al., Scientific Research Institute of Organic Intermediates and Dyes, Moscow. Translated from Zhurnal Organicheskoi Khimii, vol. 22, No. 5, pp. 1061–1065, May, 1986. Original article submitted May 13, 1985.

*Primary Examiner*—Alan L. Rotman
*Attorney, Agent, or Firm*—Curtis, Morris & Safford, P.C.

[57] ABSTRACT

3-Chloropyridines, process for their preparation, and their use in liquid-crystal mixtures A 3-chloropyridine of the formula (I)

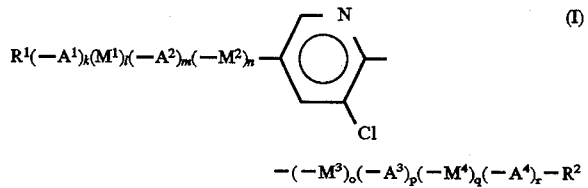

in which the symbols have the following meaning:

$R^1$ and $R^2$, independently of one another, are, for example, H or straight-chain or branched alkyl, $A^1$, $A^2$, $A^3$ and $A^4$ are identical or different and are, for example, 1,4-phenylene, pyrazine-2,5-diyl or trans-1,4-cyclohexylene, $M^1$, $M^2$, $M^3$ and $M^4$ are identical or different and are, for example, —O— or —CO—O—, $R^3$, $R^4$, $R^6$ and $R^7$, independently of one another are, for example, H or straight-chain or branched alkyl, $M^5$ is, for example, —O—CO— or a single bond, k, l, m, n, o, p, q and r are zero or one, with the proviso that the sum k+m+p+r is less than 4 and greater than zero, can advantageously be employed as a component in ferroelectric liquid-crystal mixtures.

5 Claims, No Drawings

3-CHLOROPYRIDINES, AND THEIR USE IN LIQUID-CRYSTAL MIXTURES

DESCRIPTION

The unusual combination of anisotropic and fluid behavior of liquid crystals has resulted in their use in electro-optical switching and display devices, where their electrical, magnetic, elastic and/or thermal properties can be utilized to effect changes in alignment. Optical effects can be achieved, for example, with the aid of birefringence, the inclusion of dye molecules which absorb dichroically ("guest-host mode") or by light scattering.

In order to satisfy the constantly increasing practical requirements in the various areas of application, there is a constant demand for novel improved liquid-crystal mixtures and thus also for a wide range of mesogenic compounds of various structure. This applies both to areas in which nematic LC phases are used and to those in which smectic LC phases are used.

There has been particular interest recently in ferro-electric liquid-crystalline mixtures (FLC mixtures) (see, for example, J. W. Goodby, Ferroelectric Liquid Crystals, Gordon and Breach, Philadelphia, 1991). For practical use of ferroelectric liquid crystals in electro-optical displays, chiral, tilted, smectic phases, such as $S_c^*$ phases are required [see, for example, R. B. Meyer, L. Liebert, L. Strzelecki and P. Keller, J. Physique 36, L-69 (1975)], which are stable over a broad temperature range. This aim can be achieved by means of compounds which themselves form such phases, for example $S_c^*$ phases, or by doping compounds which do not form chiral, tilted, smectic phases with optically active compounds [see, for example, M. Brunet, C. Williams, Ann. Phys. 3, 237 (1978)].

When ferroelectric liquid-crystal mixtures are used in electro-optical components, a uniform planar alignment of the liquid crystals is necessary in order to achieve a high contrast ratio. It has been found that a uniform planar alignment in the $S_c^*$ phase can be achieved if the phase sequence of the liquid-crystal mixture is, with decreasing temperature:
isotropic-nematic-smectic A-smectic C (see, for example, K. Flatischler et al., Mol. Cryst. Liq. Cryst. 131, 21 (1985); T. Matsumoto et al., p.468–470, Proc. of the 6th Int. Display Research Conf., Japan Display, 30 Sep.–2 Oct. 1986, Tokyo, Japan; M. Murakami et al., ibid, p. 344–347).

For ferroelectric (chiral smectic) liquid-crystal mixtures, the condition must additionally be satisfied that the pitch of the helix in the $S_c^*$ phase is large, i.e. greater than 5 μm, and the pitch of the helix in the N* phase is very large, i.e. greater than 10 μm, or is infinite.

The optical response time τ[μs] of ferroelectric liquid-crystal systems, which should be as short as possible, depends on the rotational viscosity of the system γ[mPas], the spontaneous polarization $P_s$[nC/cm$^2$] and the electrical field strength E[V/m], in accordance with the equation $$\tau \approx \frac{\gamma}{P_S \cdot E}$$

Since the field strength E is determined by the electrode separation in the electro-optical component and by the applied voltage, the ferroelectric display medium must have low viscosity and high spontaneous polarization in order to achieve a short response time.

Finally, in addition to thermal, chemical and photochemical stability, a small optical anisotropy Δn, preferably ≈0.13, and a low positive or preferably negative dielectric anisotropy Δε are required (see, for example, S. T. Lagerwall et al., "Ferroelectric Liquid Crystals for Displays" SID Symposium, Oct. Meeting 1985, San Diego, Calif., USA).

The totality of these requirements can generally only be satisfied by means of mixtures comprising a plurality of components. As the base (or matrix), preference is given to compounds which themselves already have the desired phase sequence I→N→$S_A$→$S_c$. Further components of the mixture are frequently added in order to reduce the melting point and to broaden the $S_c$ phase and usually also the N phase, to induce optical activity, for pitch compensation and to match the optical and dielectric anisotropy; however, the rotational viscosity, for example, should if possible not be increased.

Some of these components and also certain mixtures are already known from the prior art. However, since development in particular of ferroelectric liquid-crystal mixtures, can in no way be regarded as complete, the manufacturers of displays are interested in various mixtures. This is also the case because, inter alia, only the interaction of the liquid-crystalline mixtures with the individual components of the display devices or of the cells (for example the alignment layer) allows conclusions to be drawn on the quality of the liquid-crystalline mixtures also.

Pyridine derivatives exhibit, inter alia, a liquid-crystalline behavior with formation of a $S_c$ phase (see, for example, DE 4026223, EP 0391203, DE 3702-876-A, EP 0361157, U.S. Pat. No. 4,898,455, U.S. Pat. No. 4,765,924, DE 3701629, EP 0194153, EP 0228303, WO 86/06373, EP 0242716, EP 0239403, Zeitschrift für Organische Chemie, Band 22, Issue 5 (1986), pages 1061 to 1069, Molecular Crystals Liquid Crystals, Vol. 67 (1981), pages 241 to 252 and Liquid Crystals, Vol. 3, No. 12 (1988), pages 1643 to 1653).

However, a smectic phase of higher order which frequently occurs in these compounds impairs their use in ferroelectric liquid-crystal mixtures (T. Geelhaar, 1st International Symposium on Ferroelectric Liquid Crystals, Arcachon, 12–23 Sep. 1987).

Derivatives of 2-fluoropyridine are described in WO-91/04248, WO-91/04249 and WO-92/11241.

European Patent Application 0 573 878, which was not published before the priority data of the present application, proposes 3-fluoropyridine derivatives.

Surprisingly, it has now been found that certain derivatives of 3-chloropyridine are suitable for inducing and broadening nematic and frequently also smectic A phases in liquid-crystal mixtures.

The present invention therefore relates to 3-chloropyridine derivatives of the formula (I) and to their use as components of liquid-crystal mixtures, where at least one 3-chloropyridine of the formula (I) is employed as a component in a liquid-crystal mixture.

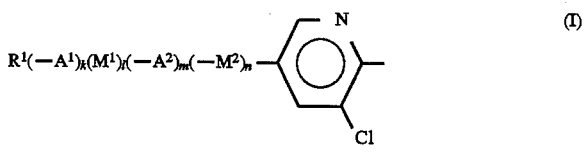

The symbols in this formula have the following meanings:
$R^1$ and $R^2$ are identical or different and are —H, —F, —Cl, —CN, —NCS, —CF$_3$, —OCF$_3$, —OCHF$_2$ or straight-chain or branched (with or without an asymmetric carbon atom) alkyl having 1 to 16 or 3 to 16 carbon atoms respectively, it also being possible for one or two non-adjacent —CH$_2$— groups to be replaced by

—O—, —S—, —CO—, —CO—O—, —O—CO—,

—CO—S—, —S—CO—, —O—CO—O—,

—CH=CH—, —C≡C—, 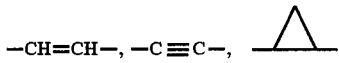

or —Si(CH$_3$)$_2$—, and it also being possible for one or more hydrogen atoms in the alkyl radical to be substituted by —F, —Cl, —Br or —CN, or are one of the following chiral groups:

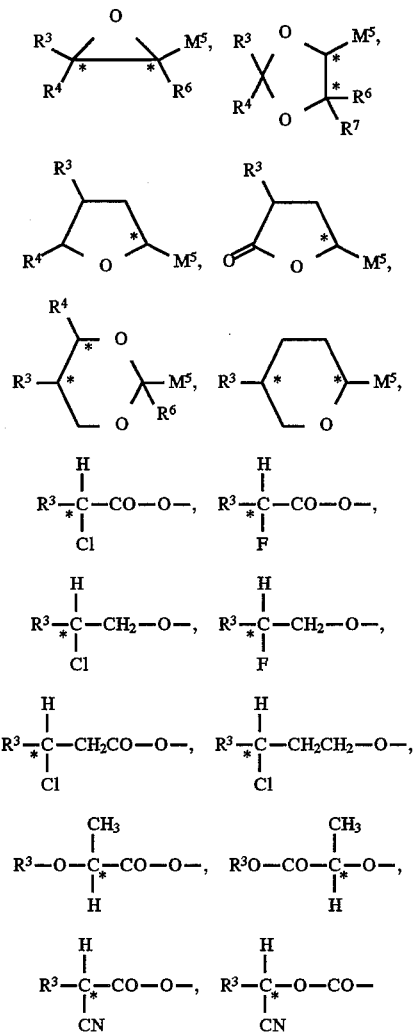

A$^1$, A$^2$, A$^3$ and A$^4$ are identical or different and are 1,4-phenylene, pyrazine-2,5-diyl, pyridazine-3,6-diyl, pyridine-2,5-diyl, pyrimidine-2,5-diyl, where one or two hydrogen atoms may be replaced by F, trans-1,4-cyclohexylene, in which one or two hydrogen atoms may in each case be replaced by CN, 1,3,4-thiadiazole-2,5-diyl, 1,3-dioxane-2,5-diyl, naphthalene-2,6-diyl, bicyclo[2.2.2]octane-1,4-diyl or 1,3-dioxaborinane-2,5-diyl;

M$^1$, M$^2$, M$^3$ and M$^4$ are identical or different and are —O—, —S—, —CO—, —CO—O—, —O—CO—, —CO—S—, —S—CO—, —O—CO—O—, —CH$_2$—O—, —O—CH$_2$—, —CH$_2$—CH$_2$—, —CH=CH— or —C≡C—;

R$^3$, R$^4$, R$^6$ and R$^7$ are identical or different and are H or straight-chain or branched alkyl having 1 to 16 or 3 to 16 carbon atoms respectively, or R$^3$ and R$^4$ together are alternatively —(CH$_2$)$_4$— or —(CH$_2$)$_5$— if bonded as substituents to a dioxolane system;

M$^5$ is —CH$_2$—O—, —CO—O—, —O—CH$_2$—, —O—CO— or a single bond;

k, l, m, n, o, p, q and r are zero or one, with the proviso that the sum k+m+p+r is less than 4 and greater than zero.

In a preferred embodiment of the invention, the symbols in the formula (I) have the following meanings:

R$^1$ and R$^2$ are identical or different and are —H, —F, —CN or straight-chain or branched (with or without an asymmetric carbon atom) alkyl having 1 to 16 or 3 to 16 carbon atoms respectively, it also being possible for one —CH$_2$— group to be replaced by

—O—, —S—, —CO—, —CO—O—, —O—CO—,

—O—CO—O—, —CH=CH—, —C≡C—, 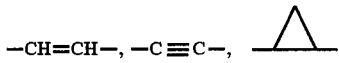

or

—Si(CH$_3$)$_2$—, or are one of the following chiral groups:

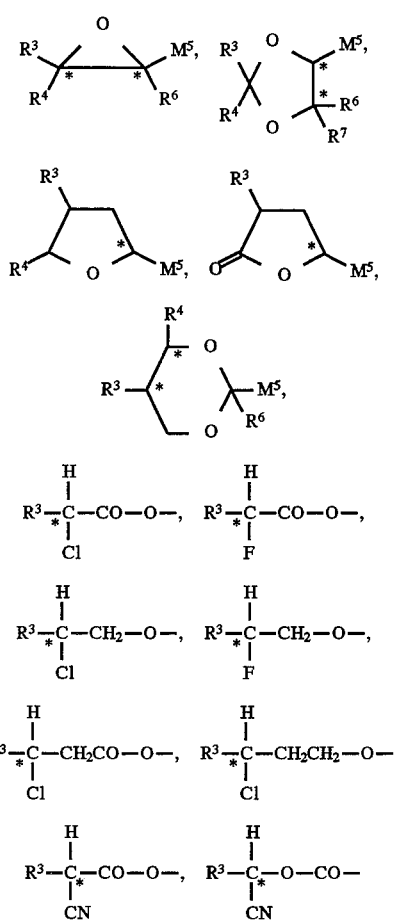

A$^1$, A$^2$, A$^3$ and A$^4$ are identical or different and are 1,4-phenylene, pyrazine-2,5-diyl, pyridazine-3,6-diyl, pyridine-2,5-diyl, pyrimidine-2,5-diyl, where one or two hydrogen atoms may in each case be replaced by F, trans-1,4-cyclohexylene, 1,3,4-thiadiazole-2,5-diyl, 1,3-dioxane-2,5-diyl, naphthalene-2,6-diyl, bicyclo[2.2.2]octane-1,4-diyl or 1,3-dioxaborinane-2,5-diyl;

$M^1$, $M^2$, $M^3$ and $M^4$, are identical or different and are —O—, —CO—, —CO—O—, —O—CO—, —CH$_2$—O—, —O—CH$_2$—, —CH$_2$—CH$_2$—, —CH=CH— or —C≡C—; $R^3$, $R^4$, $R^6$ and $R^7$ are identical or different and are H or straight-chain or branched alkyl having 1 to 10 or 3 to 10 carbon atoms respectively, or $R^3$ and $R^4$ together are alternatively —(CH$_2$)$_4$— or —(CH$_2$)$_5$— if bonded as substituents to a dioxolane system;

$M^5$ is —CH$_2$—O—, —CO—O—, —O—CH$_2$—, —O—CO— or a single bond.

Preference is furthermore given to 3-chloropyridine derivatives of the formula (I) in which the symbols have the following meanings:

$R^1$ and $R^2$ are identical or different and are —H, —F, —CN or straight-chain or branched (with or without an asymmetric carbon atom) alkyl having 1 to 10 or 3 to 10 carbon atoms respectively, it also being possible for one —CH$_2$— group to be replaced by —O—, —CO—, —CO—O—, —O—CO—, —CH=CH— or —Si(CH$_3$)$_2$—, or are one of the following chiral groups:

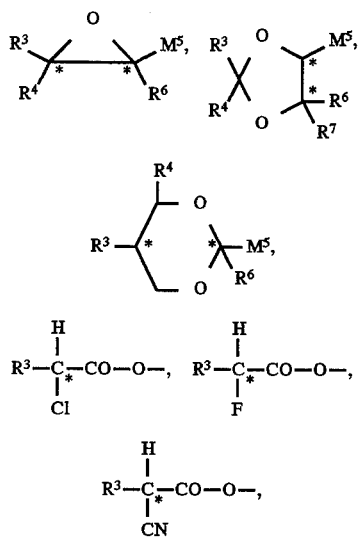

$A^1$, $A^2$, $A^3$ and $A^4$ are identical or different and are 1,4-phenylene, pyrazine-2,5-diyl, pyridazine-3,6-diyl, pyridine-2,5-diyl, pyrimidine-2,5-diyl, in which one or two hydrogen atoms may be replaced by F, trans-1,4-cyclohexylene, 1,3-dioxane-2,5-diyl, naphthalene-2,6-diyl or 1,3-dioxaborinane-2,5-diyl;

$M^1$, $M^2$, $M^3$ and $M^4$ are identical or different and are —O—, —CO—O—, —O—CO—, —O—CH$_2$—, —CH$_2$—O— or —CH=CH—;

$R^3$, $R^4$, $R^6$ and $R^7$ are identical or different and are H or straight-chain or branched alkyl having 1 to 10 carbon atoms, or $R^3$ and $R^4$ together are alternatively —(CH$_2$)$_4$— or —(CH$_2$)$_5$— if bonded as substituents to a dioxolane system;

$M^5$ is —CH$_2$—O—, —CO—O—, —O—CH$_2$—, —O—CO— or a single bond.

Particular preference is given to a 3-chloropyridine of the formula (I) in which $R^1$ and $R^2$ are identical or different and are H or alkyl having 1 to 16 carbon atoms, it also being possible for one —CH$_2$— group to be replaced by —O—, —CO—O— or —O—CO—, or are the chiral group

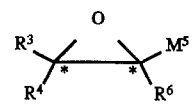

$A^1$, $A^2$, $A^3$ and $A^4$ are identical or different and are 1,4-phenylene, pyrazine-2,5-diyl, pyridazine-3,6-diyl, pyridine-2,5-diyl, pyrimidine-2,5-diyl, in which one or two hydrogen atoms may in each case be replaced by F, trans-1,4-cyclohexylene, 1,3-dioxane-2,5-diyl, naphthalene-2,6-diyl or 1,3-dioxaborinane-2,5-diyl;

$M^1$, $M^2$, $M^3$ and $M^4$ are identical or different and are —O—, —CO—O—, —O—CO—, —OCH$_2$—, —CH$_2$—O— or —CH$_2$CH$_2$—;

$R^3$, $R^4$ and $R^6$ are identical or different and are H or straight-chain alkyl having 1 to 10 carbon atoms;

$M^5$ is —CH$_2$—O— or —CO—O—.

The compounds according to the invention are chemically and photochemically stable. They have low melting points and generally have broad liquid-crystalline phases, in particular broad nematic, smectic A and smectic C phases. They can preferably be used for inducing or broadening $S_A$ and N phases in LC mixtures, in particular in ferroelectric mixtures. In particular in ferroelectric LC mixtures, sufficiently broad $S_A$ and N phases are important for good alignment of the mixture. In addition, the compounds according to the invention generally lower the melting point of LC mixtures.

In addition, the compounds of the formula (I) have a broad range of applications. Depending on the choice of substituents, these compounds can be used as base materials of which liquid-crystalline smectic, in particular ferroelectric, phases are predominantly composed; however, compounds of the formula (I) can also be added to liquid-crystalline base materials from other classes of compound in order, for example, to vary the dielectric and/or optical anisotropy and/or the viscosity and/or the spontaneous polarization and/or the tilt angle and/or the pitch of a dielectric of this type.

Liquid-crystalline compounds containing this structural element can be used to prepare both ferroelectric mixtures and nematic or chiral nematic mixtures which are suitable for use in electro-optical or fully optical elements, for example display elements, switching elements, light modulators, elements for image processing, signal processing or generally in the area of non-linear optics.

The liquid-crystal mixtures according to the invention generally comprise 2 to 20, preferably 2 to 15, components, including at least one compound of the formula (I). The mixtures preferably contain 1 to 5, particularly preferably 1 to 3, very particularly preferably 1, of the compounds according to the invention. The other constituents are preferably selected from known compounds having nematic, cholesteric and/or tilted smectic phases; these include, for example, Schiff bases, biphenyls, pyridines, thiadiazoles, difluorophenyls, terphenyls, phenylcyclohexanes, cyclohexylbiphenyls, pyrimidines, cinnamic acid esters, cholesterol esters and polycyclic esters of p-alkylbenzoic acids. In general, the commercially available liquid-crystal mixtures are already, before addition of the compound(s) according to the invention, in the form of mixtures of the various components, of which at least one is mesogenic.

The liquid-crystal mixtures generally contain from 0.1 to 70 mol %, preferably from 0.5 to 50 mol %, in particular from 1 to 25 mol %, of the 3-chloropyridine derivative(s) according to the invention.

The values for the spontaneous polarization $P_s$[nC/cm$^2$], the contrast C and the optical response time $\tau$[µs] were determined for the ready-to-use ferroelectric liquid-crystal mixtures, all measurements being carried out at a temperature of 25° C.

The $P_s$ values are measured by the method of H. Diamant et al. (Rev. Sci. Instr., 28, 30, 1957), using measurement cells having an electrode separation of 2 µm and rubbed polyimide as alignment layer. In order to determine $\tau$ and C, the measurement cell is mounted between crossed analyzer and polarizer on the rotary stage of a polarizing microscope. For determining the contrast (C), the measurement cell is positioned by rotation so that a photodiode indicates minimum light transmission (dark state). The microscope illumination is adjusted so that the photodiode indicates the same light intensity for all cells. After a switching operation, the light intensity changes (bright state) and the contrast is calculated from the ratio between the light intensities in these states.

In order to determine $\tau$ and the switching angle $\phi_{\mathit{eff}}$, the position of the stage at which light transmission is at its lowest is determined for the two switching states in the cell by rotating the stage. The difference between the two positions on the rotary stage is equal to twice the effective tilt angle. With the aid of a photodiode, the response time $\tau$ is determined by measuring the time taken for the light signal to increase from 10 to 90%. The switching voltage comprises rectangular pulses and is ±10 V/µm.

The phase transition temperatures are determined with the aid of a polarizing microscope from the changes in texture during heating. By contrast, the melting point was determined using a DSC instrument. The phase transition temperatures between the phases

| nematic | (N or N*) |
| smectic C | ($S_C$ or $S_C$*) |
| smectic A | ($S_A$ or $S_A$*) |
| crystalline | (X) | are given in °C. and the values are between the phase designations in the phase sequence.

Liquid-crystalline mixtures which contain compounds of the formula (I) are particularly suitable for use in electro-optical switching and display devices (displays). Switching and display devices (LC displays) contain, inter alia, the following constituents: a liquid-crystalline medium, outer plates (for example made of glass or plastic), coated with transparent electrodes, at least one alignment layer, spacers, an adhesive frame, polarizers and, for color displays, thin colored filter layers. Further possible components are antireflection, passivation, equalization and barrier layers and electrically non-linear elements, such as thin-film transistors (TFTs) and metal/insulator/metal (MIM) elements. The structure of liquid-crystal displays has already been described in detail in relevant monographs (for example E. Kaneko, "Liquid Crystal TV Displays: Principles and Applications of Liquid Crystal Displays", KTK Scientific Publishers, 1987, pages 12–30 and 63–172).

The compounds according to the invention can be prepared, for example, by the process outlined in Schemes 1 to 5, in which the side chains $R^1(—A^1)_k(—M^1)_l(—A^2)_m(—M^2)_n—$ and $(—M^3)_o(—A^3)_p(—M^4)_q(—A^4)_r—R^2$ are introduced into the 2- and 5-position respectively of the pyridine ring by a multi-step reaction via the intermediate 2,5-dibromo-3-chloropyridine (VI).

The starting compound in the preparation process according to the invention is 3-chloro-2-hydroxypyridine (IV), which can be prepared from 3-chloropyridine (II) via 3-chloropyridine-N-oxide (III) by the method described by M. P. Cava and B. Weinstein in the Journal of Organic Chemistry 23 (1958) on pages 1616 to 1617.

Reaction of 3-chloro-2-hydroxypyridine (IV) with bromine at temperatures between −70° C. and 150° C., in particular between −20° C. and 50° C., in an inert solvent gives 5-bromo-3-chloro-2-hydroxypyridine (V), which can be converted into 2,5-dibromo-3-chloropyridine (VI) by treatment with a brominating agent, such as phosphorus tribromide, phosphorus oxytribromide and phosphorus pentabromide, at temperatures between 50° C. and 250° C., in particular between 100° C. and 170° C.

Replacement of the bromine substituent in the 2-position of compound (VI) by a group of the formula $Z^1=(-M^3)_o(-A^3)_p(-M^4)_q(-A^4)_r-R^2$ by reaction with a metal compound of $Z^1$, for example a lithium, sodium, potassium or magnesium compound, at temperatures between −40° and 100° C., in particular between −10° and 70° C., in an inert reaction medium, for example diethyl ether, tetrahydrofuran, 1,4-dioxane, ethylene glycol diethyl ether or diethylene glycol diethyl ether, gives compounds of the formula (VII).

Cross-coupling of compound (VI) with organometallic derivatives of $Z^1$ for example Grignard, lithium and zinc derivatives, and boronic acids of $Z^1$ using transition-metal catalysts, for example dichloro[1,3-bis(diphenylphosphino)propane]nickel (II) chloride and tetrakis(triphenylphosphine)palladium(0), at temperatures between −40° and 200° C., in particular between −10° and 100° C., in reaction media such as benzene/ethanol/water for reaction with boronic acids of $Z^1$ and, for example, diethyl ether or tetrahydrofuran for the reaction with Grignard, lithium and zinc derivatives of $Z^1$ likewise gives compounds of the type (VII).

Cross-coupling of compounds of type (VII) with organometallic derivatives of $Z^2$, for example Grignard, lithium and zinc derivatives, and boronic acids of $Z^2$ using transition-metal catalysts, for example dichloro[1,3-bis(diphenylphosphino)propane]nickel(II) chloride and tetrakis(triphenylphosphine)palladium(0) at temperatures between −40° and 200° C., in particular between −10° and 100° C., in reaction media such as benzene/ethanol/water for the reaction with boronic acids of $Z^2$ and diethyl ether or tetrahydrofuran for the reaction with Grignard, lithium and zinc derivatives of $Z^2$ gives 3-chloropyridines (I).

3-Chloropyridines of type (VII) can be converted into 3-chloro-5-lithiopyridines of the formula (VIII) by treatment with an alkyllithium compound, such as n-butyllithium, tert-butyllithium or methyllithium, at temperatures between −100° and 50° C., in particular between −80° and 10° C., in an inert reaction medium, for example diethyl ether, tetrahydrofuran or ethylene glycol dimethyl ether. 5-Lithiopyridines of the formula (VIII) are capable of undergoing reaction with electrophilic compounds, which gives 3-chloropyridines of the formula (I), either directly or via further intermediates (compounds (IX), (X), (XI), (XII) and (XIII)).

Thus, 3-chloro-5-lithiopyridines (VIII) give 3-chloro-5-pyridinecarboxylic acids of the formula (IX) after treatment with carbon dioxide at temperatures between −100° and 50° C., in particular between −80° and 10° C., in an inert reaction medium, for example diethyl ether, tetrahydrofuran or ethylene glycol diethyl ether. Species (IX) can be converted into compounds of the formula (I) by methods known per se from the literature (see, for example, Houben-Weyl, Methoden der Organischen Chemie [Methods of Organic Chemistry], Georg Thieme Verlag, Stuttgart), either directly by esterification using alcohols of $Z^3$ with the aid of suitable condensation agents, for example carbodiimides, to give 3-chloropyridines (I), or, after reduction to 3-chloro-5-hydroxymethylpyridines (X) by means of suitable reducing agents, for example complex hydrides, by esterification with carboxylic acids or carboxylic halides or chloroformic acid derivatives of $Z^3$ or by etherification by means of alcohols or halides of $Z^3$.

The reaction of compounds of type (VIII) with nitriles, carboxylic halides and formylmethyl derivatives of $Z^3$ at temperatures between $-100°$ and $50°$ C., in particular between $-80°$ and $10°$ C., in an inert reaction medium, for example diethyl ether, tetrahydrofuran or ethylene glycol diethyl ether, results directly in 3-chloropyridines of the formula (I). Olefinic 3-chloropyridines (I) can be converted into saturated species (I) by hydrogenation of the olefinic double bond by methods known per se from the literature (see, for example, Houben-Weyl, Methoden der Organischen Chemie [Methods of Organic Chemistry], Georg Thieme Verlag, Stuttgart).

Reaction of 3-chloro-5-lithiopyridines (VIII) with formamides at temperatures between $-100°$ and $50°$ C., in particular between $-80°$ and $10°$ C., in an inert reaction medium, for example diethyl ether, tetrahydrofuran or ethylene glycol diethyl ether, gives 3-chloro-5-formylpyridines (XI), which give 3-chloropyridines of type (I) after acid-catalyzed acetalization using 2-$Z^4$-1,3-propanediols by methods known per se from the literature (see, for example, Houben-Weyl, Methoden der Organischen Chemie [Methods of Organic Chemistry], Georg Thieme Verlag, Stuttgart).

Successive treatment of the 3-chloro-5-lithiopyridine (VIII) with trialkyl borates at temperatures between $-100°$ and $50°$ C., in particular between $-80°$ and $10°$ C., and aqueous acid at temperatures between $-10°$ and $50°$ C., in particular between $10°$ and $30°$ C., in an inert reaction medium, for example diethyl ether, tetrahydrofuran or ethylene glycol diethyl ether, gives 3-chloro-5-pyridineboronic acids of the formula (XII).

The boronic acids (XII) can be subjected to coupling reactions with halides of $Z^3$ using a transition-metal catalyst, for example tetrakis (triphenylphosphine)palladium(0), at temperatures between $30°$ and $200°$ C., in particular between $50°$ and $100°$ C., in reaction media such as benzene/ethanol/water, in order to prepare compounds of type (I).

3-Chloropyridines (I) are furthermore obtained from the boronic acids (XII) by esterification thereof using 2-$Z^4$-1,3-propanediols by methods known per se from the literature (see, for example, Houben-Weyl, Methoden der Organischen Chemie [Methods of Organic Chemistry], Georg Thieme Verlag, Stuttgart).

Oxidation of the boronic acids (XII) using peroxides, for example hydrogen peroxide, at temperatures between $10°$ and $100°$ C. in particular between $30°$ and $70°$ C., in reaction media such as diethyl ether or tetrahydrofuran, gives the 3-chloro-5-hydroxypyridines (XIII), which can be converted into 3-chloropyridines of the formula (I) by methods known from the literature (see, for example, Houben-Weyl, Methoden der Organischen Chemie [Methods of Organic Chemistry], Georg Thieme Verlag, Stuttgart) by esterifica tion by means of carboxylic acids or chloroformic acid derivatives or carboxylic halides of $Z^3$ or by etherification by means of alcohols or halides of $Z^3$.

Scheme 1:

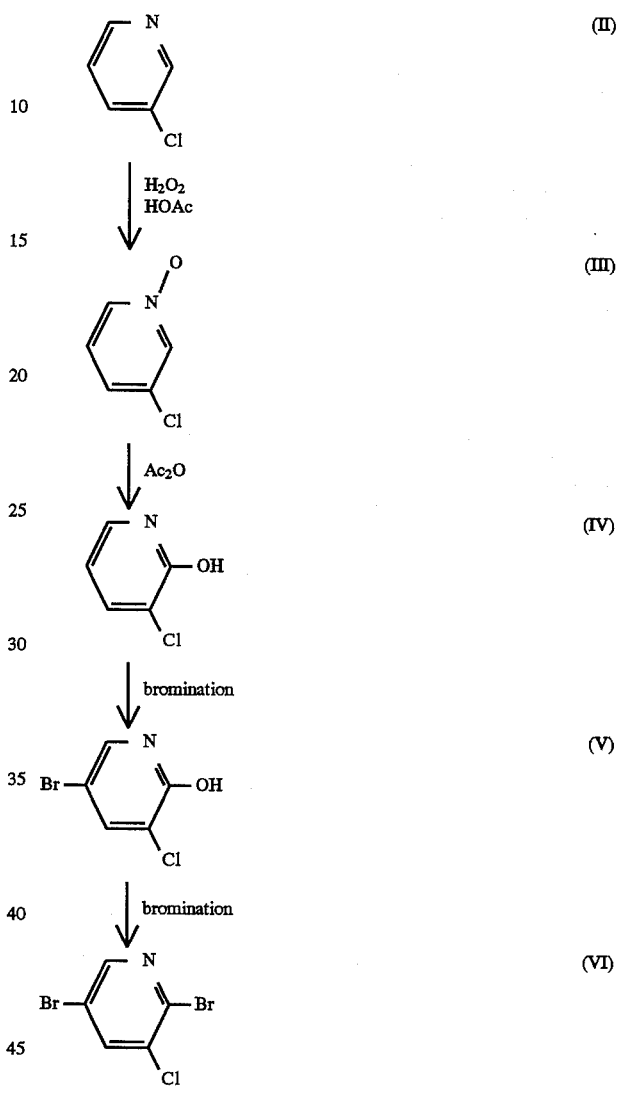

Scheme 2:

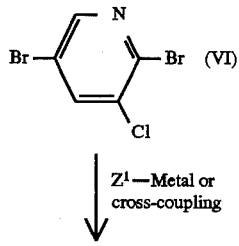

-continued
Scheme 2:
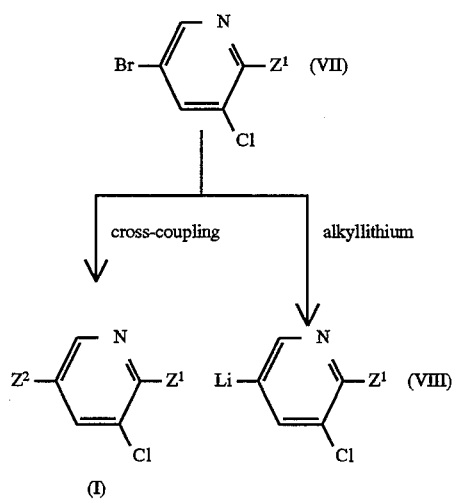
$Z^1 = (-M^3)_o(-A^3)_p(-M^4)_q(-A^4)_r-R^2 \quad Z^2 = R^1(-A^1)_k(-M^1)_l(-A^2)_m(-M^2)_n-$
Scheme 3:
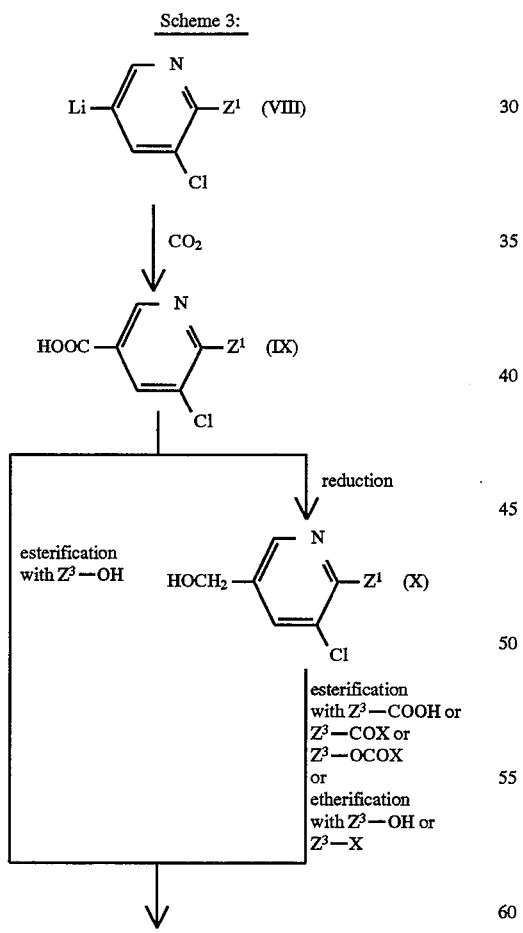
-continued
Scheme 3:
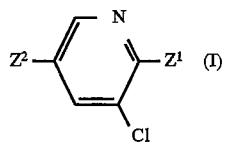
$Z^1$ and $Z^2$, see Scheme 2 $Z^3 = R^1(-A^1)_k(-M^1)_l(-A^2)_m-$
X=Cl, Br, I Scheme 4:
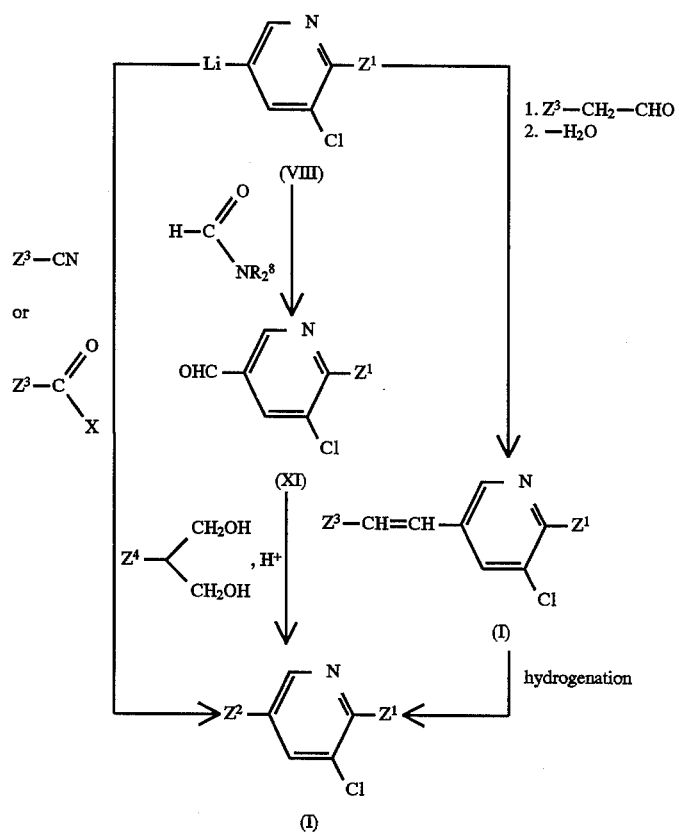
$Z^1$, $Z^2$, $Z^3$ and X, see Schemes 2 and 3. $Z^4=R^1(-A^1)_k(-M^1)_l$
$R^8$=straight-chain or branched alkyl having 1 to 10 carbon atoms
Scheme 5:
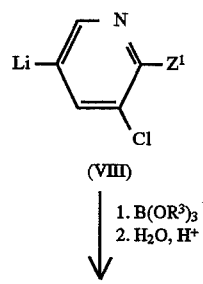

-continued
Scheme 5:

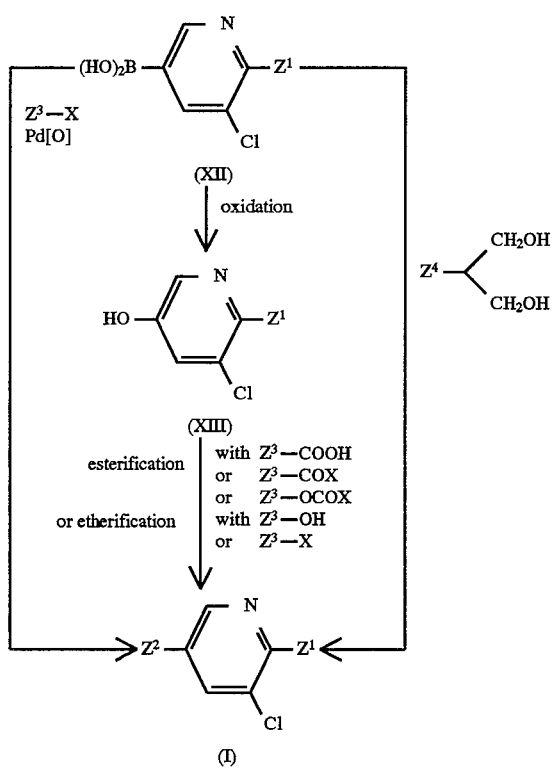

$Z^1$, $Z^2$, $Z^3$, $Z^4$, $R^8$ and X, see Schemes 2, 3 and 4.

The starting compounds for the later groups $Z^1$ and $Z^2$ are synthesized by methods known per se from the literature, as described in standard works on organic synthesis, for example Houben-Weyl, Methoden der Organischen Chemie, Georg Thieme Verlag, Stuttgart.

The preparation is carried out under reaction conditions which are known and suitable for said reactions. Use may also be made here of variants which are known per se, but are not described here in greater detail.

For example, reference is made to DE-A 23 44 732, 24 50 088, 24 29 093, 25 02 904, 26 36 684, 27 01 591 and 27 52 975 for compounds containing 1,4-cyclohexylene and 1,4-phenylene groups; DE-A 26 41 724 for compounds containing pyrimidine-2,5-diyl groups; DE-A 40 26 223 and EP-A 0 391 203 for compounds containing pyridine-2,5-diyl groups; DE-A 32 31 462 for compounds containing pyridazine-3,6-diyl groups; N. Miyaura, T. Yanagi and A. Suzuki in Synthetic Communications 11 (1981), 513–519, DE-C-3 930 663, M. J. Sharp, W. Cheng, V. Snieckus in Tetrahadron Letters 28 (1987), 5093 ff.; G. W. Gray in J. Chem. Soc. Perkin Trans. II, 1989, 2041 ff. and Mol. Cryst. Liq. Cryst. 172 (1989), 165 ff.; 204 (1991) 43 ff. and 91 ff.; EP-A 0 449 015; WO 89/12039; WO 89/03821; EP-A 0 354 434 for the direct linking of aromatics and heteroaromatics; DE-A 32 01 721 for compounds containing —$CH_2$—$CH_2$— bridges, and Koji Sero etal. in Liquid Crystals 8 (1990) 861–870 for compounds containing —C≡C— bridges. The preparation of disubstituted pyridines, disubstituted pyrazines, disubstituted pyrimidines and disubstituted pyridazines is described, for example, in the appropriate volumes of the series "The Chemistry of Heterocyclic Compounds" by A. Weissberger and E. C. Taylor (editors).

If desired, the starting materials can also be prepared in situ by not isolating them from the reaction mixture, but instead immediately converting them further into the compounds of the formula (I).

Reference may be made to EP-A 0 355 008 for the synthesis of compounds of the formula (I) in which the side chains, $R^1$ and $R^2$, contain silyl groups, to EP-A 0 318 423 for cyclopropyl side chains, to EP-A 0 263 437 or EP-A 0 292 954 for side chains containing optically active oxirane ethers or esters, to EP-A 0 351 746 or EP-A 0 361 272 for side chains containing optically active dioxolane ethers or esters, to EP-A 0 355 561 for side chains containing optically active tetrahydrofuran-2-carboxylates, and to P. Keller, Ferroelectrics 58 (1984) 3, for side chains containing optically active alkyl groups.

The invention is described in greater detail by the examples below:

EXAMPLE 1

3-Chloro-5-octyl-2-(4-octyloxyphenyl)pyridine 10.5 ml (203.0 mmol) of bromine are added dropwise at 0° C. to 23.9 g (184.5 mmol) of 3-chloro-2-hydroxypyridine in 240 ml of dimethylformamide, and the mixture is stirred at room temperature for 2 hours. 200 ml of water are subsequently added, and 30 g of sodium sulfite in 100 ml of water are added dropwise. After 15 minutes, the mixture is extracted three times with 200 ml of dichloromethane in each case, the combined organic phases are dried over sodium sulfate and filtered, and the filtrate is evaporated to dryness, giving 36.58 g of 5-bromo-3-chloro-2-hydroxypyridine.

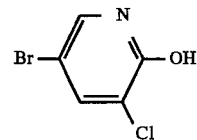

m.p.: 168° C. (decomp.)

36.0 g (172.7 mmol) of 5-bromo-3-chloro-2-hydroxypyridine are stirred at 160° C. for 6 hours in 320 ml of phosphorus tribromide. The reaction mixture is cooled to room temperature and poured carefully into ice water. After 2 hours, the mixture is extracted three times with 500 ml of dichloromethane in each case. The combined organic phases are washed with sodium bicarbonate solution until neutral, dried over $Na_2SO_4$ and filtered, and the filtrate is evaporated to dryness. Chromatographic purification (silica gel/dichloromethane) gives 20.53 g of 3-chloro-2,5-dibromopyridine.

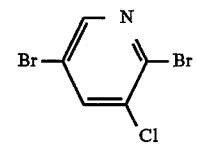

m.p.: 40°–41° C.

A solution of the Grignard compound of 2.40 g (99.0 mmol) of magnesium and 25.56 g (89.6 mmol) of 4-octyloxybromobenzene in 250 ml of tetrahydrofuran is prepared at 60° C. for 3 hours and is then added dropwise to a solution, cooled to –70° C., of 18.62 g (99.00 mmol) of triisopropyl borate in 100 ml of tetrahydrofuran, and the mixture is stirred overnight. 130 ml of 10% strength hydrochloric acid are subsequently added dropwise, and the mixture is stirred at room temperature for 1 hour and partitioned between sodium chloride solution and ether, and the organic phase is washed with sodium chloride solution, dried over sodium sulfate and evaporated, giving 21.26 g of 4-octyloxybenzeneboronic acid.

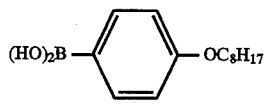

m.p.: 72°–73° C.

10.0 g (37.0 mmol) of 3-chloro-2,5-dibromopyridine, 11.11 g (44.4 mmol) of 4-octyloxybenzeneboronic acid, 7.85 g (74.0 mmol) of sodium carbonate and 0.46 g (0.4 mmol) of tetrakis(triphenylphosphine)palladium(0) are heated at 80° C. for 18 hours in 125 ml of toluene, 60 ml of ethanol and 60 ml of water. The mixture is subsequently partitioned between aqueous sodium chloride solution and ether, the organic phase is washed with aqueous sodium chloride solution, dried over sodium sulfate and evaporated, and the product is purified by chromatography (silica gel, dichloromethane:hexane =4:1), giving 9.93 g of 5-bromo-3-chloro-2-(4-octyloxyphenyl)pyridine.

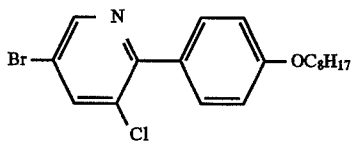

A solution of the Grignard compound of 0.30 g (12.30 mmol) of magnesium and 2.16 g (11.18 mmol) of octyl bromide in 10 ml of tetrahydrofuran is prepared at 50° C. for 2 hours and is added dropwise to a solution, cooled to −10° C., of 2.22 g (5.59 mmol) of 5-bromo-3-chloro-2-(4-octyloxyphenyl)pyridine and 0.03 g (0.06 mmol ) of [1,3-bis(diphenylphosphino)propane]-nickel(II) chloride in 60 ml of tetrahydrofuran, and the mixture is stirred at −10° C. for 3 hours. The mixture is subsequently partitioned between ether and aqueous ammonium chloride solution, and the organic phase is washed twice with aqueous sodium chloride solution, dried over sodium sulfate and evaporated to dryness. Chromatographic purification (silica gel/ dichloromethane:hexane 7:3) gives 1.89 g of 3-chloro-5-octyl-2- (4-octyloxyphenyl)pyridine.

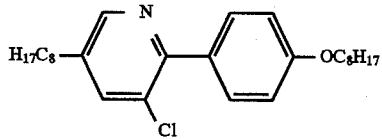

EXAMPLE 2

3-Chloro-5-octyloxy-2-(4-octyloxyphenyl)-pyridine 18.9 ml (30.30 mmol) of 1.6M n-BuLi solution in n-hexane are added dropwise at 0° C. to 4.50 g (12.10 mmol) of 5-bromo-3-chloro-2-(4-octyloxyphenyl)pyridine and 2.7 ml (24.20 mmol) of trimethyl borate in 70 ml of tetrahydrofuran, and the mixture is stirred at 0° C. for 0.5 hour. The mixture is subsequently acidified by means of dilute hydrochloric acid and partitioned between aqueous sodium chloride solution and ether, the organic phase is washed with sodium chloride solution, dried over sodium sulfate and filtered, and the filtrate is evaporated. The dry residue is dissolved in 100 ml of tetrahydrofuran and refluxed for 2 hours with 5 ml of 35% strength hydrogen peroxide. After the mixture has been cooled to 0° C., 6.3 g of $Na_2SO_3$ in 45 ml of water are added dropwise, and the mixture is stirred at room temperature for a quarter of an hour. The mixture is subsequently partitioned between ether and aqueous sodium chloride solution, the organic phase is washed with sodium chloride solution, dried over sodium sulfate and filtered, and the filtrate is evaporated to dryness. Chromatographic purification (silica gel, dichloromethane-:ethyl acetate=4:1) gives 2.35 g of 3-chloro-5-hydroxy-2-(4-octyloxyphenyl)pyridine.

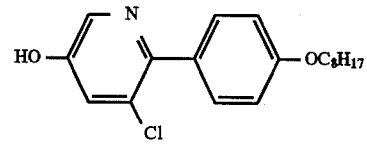

m.p.: 128°–129.5° C.

0.6 ml (3.8 mmol) of diethyl azodicarboxylate is added dropwise at 0° C. to 1.00 g (3.80 mmol) of triphenylphosphine in 15 ml of tetrahydrofuran, and the mixture is stirred at room temperature for 30 minutes. 0.78 g (2.5 mmol) of 3-chloro-5-hydroxy-2-(4-octyloxyphenyl)-pyridine and 0.6 ml (3.8 mmol) of 1-octanol are subsequently added. After a reaction time of 18 hours at room temperature, the solvent is removed by distillation and the residue is purified by chromatography (silica gel, dichloromethane). Recrystallization from acetonitrile gives 0.63 g of 3-chloro-5-octyloxy-2-(4-octyloxyphenyl)pyridine.

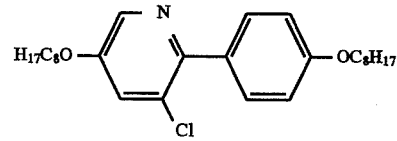

The compound has the phase sequence: X 32.2 (6.5) N 17 I.

EXAMPLE 3

3-Chloro-2-(4-octyloxyphenyl)pyridin-5-yl octanoate 1.2 ml (7.1 mmol) of octanoyl chloride are added dropwise at 0° C. to 1.57 g (4.7 mmol) of 3-chloro-5-hydroxy-2-(4-octyloxyphenyl)pyridine in 20 ml of pyridine, and the mixture is stirred at 0° C. for 3 hours. The mixture is subsequently poured into ice water and filtered, and the residue is purified by chromatography (silica gel/ hexane-:ethyl acetate 9:1) and by recrystallization from acetonitrile, giving 1.34 g of 3-chloro-2-(4-octyloxyphenyl)pyridin-5-yl octanoate.

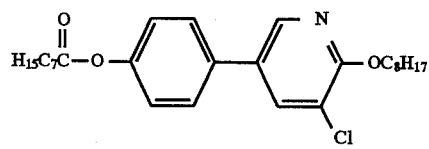

EXAMPLE 4

3-Chloro-2-octyloxy-5-(4-octyloxyphenyl)-pyridine

Lithium octanoate (prepared in advance from 13.02 g (100.00 mmol) of 1-octanol and 69 ml (110.00 mmol) of a 1.6 molar n-butyllithium solution in n-hexane in 40 ml of tetrahydrofuran at 0° C.) and 27.13 g (100.00 mmol) of 2,5-dibromo-3-chloropyridine are refluxed for 7 hours in 40 ml of tetrahydrofuran. The mixture is subsequently partitioned between aqueous sodium chloride solution and ether, the ether phase is washed twice with aqueous sodium chloride solution, dried over sodium sulfate and filtered, and the filtrate is freed from the solvent. Chromatographic purification (silica gel/hexane:ethyl acetate 9:1) gives 18.19 g (59.80 mmol) of 5-bromo-3-chloro-2-octyloxypyridine.

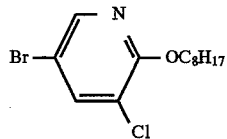

3.16 g (9.86 mmol) of 5-bromo-3-chloro-2-octyloxypyridine, 2.47 g (9.86 mmol) of 4-octyloxybenzeneboronic acid, 0.11 g (0.10 mmol) of tetrakis(triphenylphosphine)-palladium(0) and 2.09 g (19.72 mmol) of sodium carbonate are heated at 80° C. for 3 hours in 90 ml of toluene, 60 ml of ethanol and 30 ml of water. The mixture is subsequently partitioned between aqueous sodium chloride solution and ether, the organic phase is washed with aqueous sodium chloride solution, dried over sodium sulfate and evaporated, and the product is purified by chromatography (silica gel/hexane:ethyl acetate 9:1), giving 2.85 g of 3-chloro-2-octyloxy-5-(4-octyloxyphenyl)pyridine.

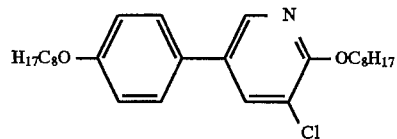

EXAMPLE 5

3-Chloro-5-octyloxy-2-[4-(octyloxyphenyl)-phenyl]pyridine

The preparation is carried out analogously to Example 2.

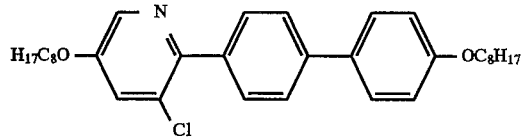

EXAMPLE 6

3-Chloro-2,5-di(4-octyloxyphenyl)pyridine 2.00 g (5.40 mmol) of 5-bromo-3-chloro-2-(4-octyloxyphenyl)pyridine, 1.50 g (6.00 mmol) of 4-octyloxybenzeneboronic acid, 0.07 g (0.6 mmol) of tetrakis(triphenylphosphine)palladium(0) and 1.3 g (12.00 mmol) of sodium carbonate are heated at 80° C. for 3 hours in 20 ml of toluene, 10 ml of ethanol and 10 ml of water. The mixture is subsequently partitioned between aqueous sodium chloride solution and ether, the organic phase is washed with aqueous sodium chloride solution, dried over sodium sulfate and evaporated, and the product is purified by chromatography (silica gel/dichloromethane), giving 1.38 g of 3-chloro-2,5-di(4-octyloxyphenyl)pyridine.

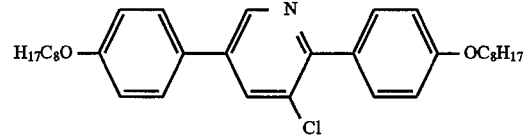

The compound has the phase sequence:
X 77 (61) $S_A$ 98N 113 I.

EXAMPLE 7

3-Chloro-2-octyloxy-5-[4-(4-octyloxyphenyl)-phenyl]pyridine

The preparation is carried out analogously to Example 4.

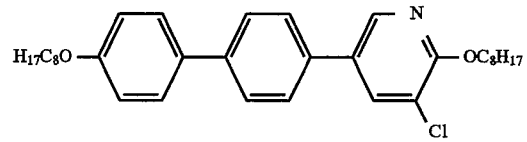

EXAMPLE 8

3-Chloro-2-(4-octyloxyphenyl)pyridin-5-yl trans-4-pentylcyclohexanecarboxylate 0.78 g (2.50 mmol) of 3-chloro-5-hydroxy-2-(4-octyloxyphenyl)pyridine, 0.52 g (2.50 mmol) of dicyclohexylcarbodiimide, 0.50 g (2.50 mmol) of trans-4-pentylcyclohexanecarboxylic acid and 0.01 g of 4-(N,N-dimethylamino)-pyridine are stirred at room temperature for 18 hours in 20 ml of dichloromethane. Filtration, evaporation to dryness and chromatographic purification (silica gel/hexane:ethyl acetate 8:2) and recrystallization from acetonitrile give 0.28 g of 3-chloro-2-(4-octyloxyphenyl)pyridin-5-yl trans-4-pentylcyclohexanecarboxylate.

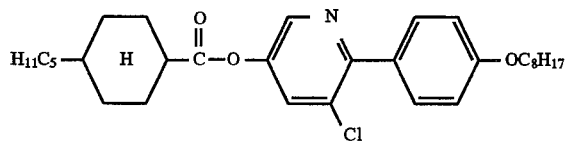

The compound has the phase sequence:
X 64.3 (1.0) N 118.7 I.

EXAMPLE 9

4-(3-chloro-5-octylpyridin-2-yl)phenyl trans-4-pentylcyclohexanecarboxylate 11.06 g (162.5 mmol) of imidazole in 30 ml of dimethylformamide are added dropwise at room temperature to 35.24 g (130.0 mmol) of tert-butylchlorodiphenylsilane and 11.25 g (65.0 mmol) of 4-bromophenol in 150 ml of dimethylformamide. After the reaction mixture has been stirred at room temperature for 1 hour, it is poured into 1000 ml of 5% strength aqueous sodium bicarbonate solution and extracted twice with 400 ml of dichloromethane, the organic phase is washed with aqueous sodium chloride solution, dried over sodium sulfate and filtered, and the filtrate is evaporated to dryness. Chromatographic purification (silica gel/hexane: ethyl acetate 8:2) gives 23.40 g of 4-bromophenyl tert-butyldiphenylsilyl ether.

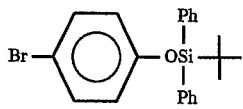

4-tert-Butyldiphenylsilyloxybenzeneboronic acid is prepared analogously to Example 1 from 4-bromophenyl tert-butyldiphenylsilyl ether.

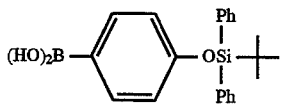

5-Bromo-2-(4-tert-butyldiphenylsilyloxyphenyl)-3-chloropyridine is prepared analogously to Example 1 from 2,5-dibromo-3-chloropyridine and 4-tert-butyldiphenylsilyloxybenzeneboronic acid.

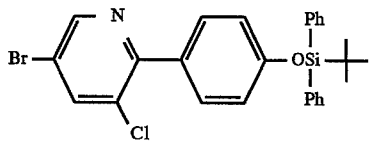

2-(4-tert-Butyldiphenylsilyloxyphenyl)-3-chloro-5-hydroxypyridine is prepared analogously to Example 2 from 5-bromo-2-(4-tert-butyldiphenylsilyloxyphenyl)-3-chloropyridine.

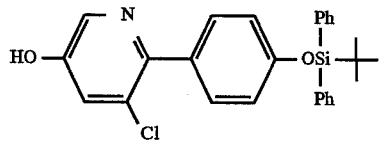

2-(tert-Butyldiphenylsilyloxyphenyl)-3-chloro-5-octyloxypyridine is prepared analogously to Example 2 from 2-(4-tert-butyldiphenylsilyloxyphenyl) -3-chloro-5-hydroxypyridine and octanol.

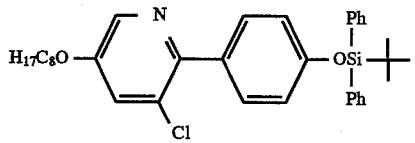

4.30 g (8.00 mmol) of 2-(4-tert-butyldiphenylsilyloxyphenyl)-3-chloro-5-octyloxypyridine are stirred at room temperature for 2 hours with 16 ml of a 1-molar tetrabutylammonium fluoride solution in tetrahydrofuran in 50 ml of tetrahydrofuran. Agueous sodium chloride solution is subsequently added, the mixture is extracted with ether, the ether phase is washed with aqueous sodium chloride solution, dried over sodium sulfate and evaporated to dryness, and the product is purified by chromatography (silica gel/hexane:ethyl acetate 8:2), giving 2.16 g of 3-chloro-2-(4-hydroxyphenyl)-5-octyloxypyridine.

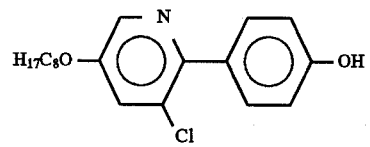

1.16 g (3.50 mmol) of 3-chloro-2-(4-hydroxyphenyl)-5-octyloxypyridine, 0.72 g (3.50 mmol) of dicyclohexylcarbodiimide, 0.69 g (3.50 mmol) of trans-4-pentylcyclohexanecarboxylic acid and 0.02 g of 4-(N,N-dimethylamino)pyridine are stirred at room temperature for 3 hours in 20 ml of dichloromethane. Filtration, evaporation to dryness, chromatographic purification (silica gel/hexane:ethyl acetate 8:2) and recrystallization from n-hexane give 1.00 g of 4-(3-chloro-5-octylpyridin-2-yl) phenyl trans-4-pentylcyclohexanecarboxylate.

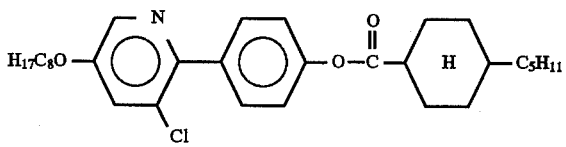

EXAMPLE 10

3-Chloro-5-octyloxy-2-[4-(trans-4-pentylcyclohexyl) phenyl]pyridine 4-(Trans-4-pentylcyclohexyl)benzeneboronic acid is prepared analogously to Example 1 from 4-(trans-4-pentylcyclohexyl)bromobenzene.

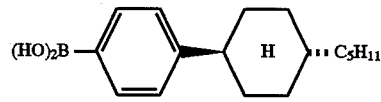

5-Bromo-3-chloro-2-[4-(trans-4-pentylcyclohexyl) phenyl]-pyridine is prepared analogously to Example 1 from 4-(trans-4-pentylcyclohexyl)benzeneboronic acid and 2,5-dibromo-3-chloropyridine.

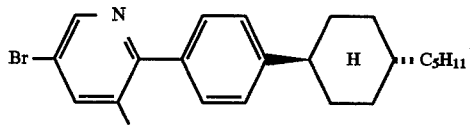

3-Chloro-5-hydroxy-2-[4-(trans-4-pentylcyclohexyl)-phenyl]pyridine is obtained analogously to Example 2 from 5-bromo-3-chloro-2-[4-(trans-4-pentylcyclohexyl)phenyl]-pyridine.

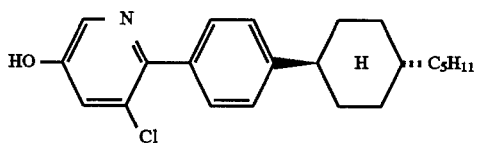

3-Chloro-5-octyloxy-2-[4-(trans-4-pentylcyclohexyl)-phenyl]pyridine is obtained analogously to Example 2 from octanol and 3-chloro-5-hydroxy-2-[4-(trans-4-pentylcyclohexyl)phenyl]pyridine.

EXAMPLE 11

3-Chloro-2-octyloxy-5-[4-(trans-4-pentylcyclohexyl)phenyl]pyridine

The preparation is carried out analogously to Example 4.

EXAMPLE 12

3-Chloro-5-octyloxy-5-(6-octyloxynaphthalen-2-yl)pyridine

The preparation is carried out analogously to Example 4.

EXAMPLE 13

3-Chloro-5-octyloxy-2-(6-octyloxynaphthalen-2-yl)pyridine

The preparation is carried out analogously to Example 10.

EXAMPLE 14

[(2S,3S)-3-Butyloxiran-2-yl]methyl 3-chloro-2-(4-octyloxyphenyl)pyridin-5-yl ether 60 ml (3.80 mmol) of diethyl azodicarboxylate are added dropwise at 0° C. to 1.00 g (3.80 mmol) of triphenylphosphine in 15 ml of tetrahydrofuran, and the mixture is stirred at room temperature for 30 minutes. 0.78 g (2.50 mmol) of 3-chloro-5-hydroxy-2-(4-octyloxyphenyl)-pyridine and 0.50 g (3.80 mmol) of 2-[(2S,3S)-3-butyloxiranyl]methanol are subsequently added. After a reaction time of 18 hours at room temperature, the solvent is removed by distillation and the residue is purified by chromatography (silica gel/hexane:ethyl acetate 8:2). Recrystallization from hexane: ethyl acetate (8:2) gives 0.43 g of [(2S,3S)-3-butyloxiran-2-yl]methyl 3-chloro-2-(4-octyloxyphenyl)pyridin-5-yl ether.

$[\alpha]_D^{20}(CH_2Cl_2) = -16.3$

The compound has the phase sequence:

$T_G$–47N 11.6 I.

EXAMPLE 15

[(2S,3S)-3-Butyloxiran-2-yl]methyl 4-(3-chloro-5-octyloxypyridin-2-yl)phenyl ether 0.91 g (5.25 mmol) of diethyl azodicarboxylate is added dropwise at 0° C. to 1.37 g (5.25 mmol) of triphenylphosphine in 20 ml of tetrahydrofuran, and the mixture is stirred at 0° C. for 30 minutes. 1.17 g (3.50 mmol) of 3-chloro-2-(4-hydroxyphenyl)-5-octyloxypyridine and 0.75 g (5.25 mmol) of 2-[(2S,3S)-3-butyloxiran-2-yl]-methanol are subsequently added. After a reaction time of 18 hours at room temperature, the solvent is removed by distillation and the residue is purified by chromatography (silica gel/hexane:ethyl acetate 8:2). Recrystallization from hexane gives 0.85 g of [(2S,3S)-3-butyloxiran-2-yl]methyl 4-(3-chloro-5-octyloxypyridin-2-yl)phenyl ether.

EXAMPLE 16

[(2S,3S)-3-Butyloxiran-2-yl]methyl 3-chloro-2-(4-(trans-4-pentylcyclohexyl)phenyl)-pyridin-5-yl ether The preparation is carried out analogously to Example 14.

Use examples

A liquid-crystal mixture comprises:

| | mol % |
|---|---|
| $C_8H_{17}$—pyridine—O—$C_6H_{13}$ | 13.41 |

| | mol % |
|---|---|
| C₈H₁₇—O—[pyridine N,N]—[phenyl]—O—C₈H₁₇ | 6.19 |
| C₈H₁₇—O—[pyridine N,N]—[phenyl]—O—C₄H₉ | 14.14 |
| C₈H₁₇—O—[pyridine N,N]—[phenyl]—O—C₁₀H₂₁ | 11.25 |
| C₈H₁₇—[pyridine N,N]—[phenyl]—O—C₈H₁₇ | 19.25 |
| C₈H₁₇—[pyridine N,N]—[phenyl]—O—C₆H₁₃ | 21.45 |
| C₈H₁₇—[pyridine N,N]—[phenyl]—O—C₁₀H₂₁ | 14.30 | and has the phase sequence X 1 (−6) $S_c$ 64 $S_A$ 77N 81 I

Use Example 1

Addition of 10 mol % of the novel substance from Example 6 to the above mixture gives a mixture having the phase sequence X 2 (−13) $S_c$ 55 $S_A$ 74N 83 I A broadening of the $S_A$ and N phases is evident.

Use Example 2

Addition of 10 mol % of the novel substance from Example 2 to the above mixture gives a mixture having the phase sequence X −1 (−12) $S_c$ 48 $S_A$ 64N 75 I A broadening of the $S_A$ and N phases is evident. In addition, the melting point is lowered.

Use Example 3

A base mixture comprises

| | mol % |
|---|---|
| C₈H₁₇—O—[pyridine N,N]—[phenyl]—O—C₆H₁₃ | 25.33 |
| C₈H₁₇—O—[pyridine N,N]—[phenyl]—O—C₈H₁₇ | 11.69 |
| C₈H₁₇—O—[pyridine N,N]—[phenyl]—O—C₄H₉ | 26.72 |
| C₈H₁₇—O—[pyridine N,N]—[phenyl]—O—C₁₀H₂₁ | 21.24 |
| C₁₀H₂₁—[pyridine N,N]—[phenyl]—O—C(=O)—[cyclohexyl H]—C₅H₁₁ | 15.00 | and has the phase sequence

X 12.5 (1.6) $S_c$ 83 $S_A$ 95N 100 I

Addition of 10 mol % of the novel substance from Example 14 to the base mixture gives a mixture having the phase sequence X 3.2 (−9.8) $S_c$ 68 $S_A$ 76N 95 I A broadening of the N phase and a lowering of the melting point are evident.

We claim:

1. A 3-chloropyridine compound of the formula (I)

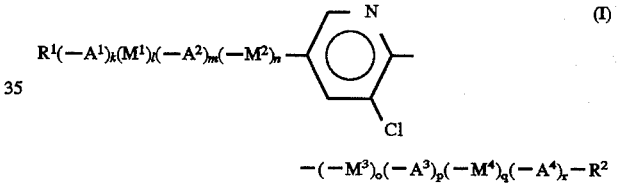

$$R^1(-A^1)_k(M^1)_l(-A^2)_m(-M^2)_n-$$
$$-(-M^3)_o(-A^3)_p(-M^4)_q(-A^4)_r-R^2$$

in which the symbols have the following meanings:

$R^1$ and $R^2$ are identical or different and are —H, or straight-chain or branched (with or without an asymmetric carbon atom) alkyl having 1 to 16 carbon atoms, it also being possible for one or two non-adjacent —CH₂—groups to be replaced by

—O—, —CO—O—, —O—CO—, —O—CO—O—,

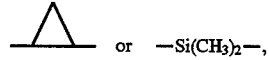 or —Si(CH₃)₂—, and optionally wherein one or more hydrogen atoms in the alkyl radical is substituted by —F, or are one of the following chiral groups:

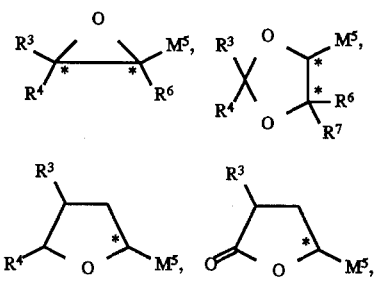

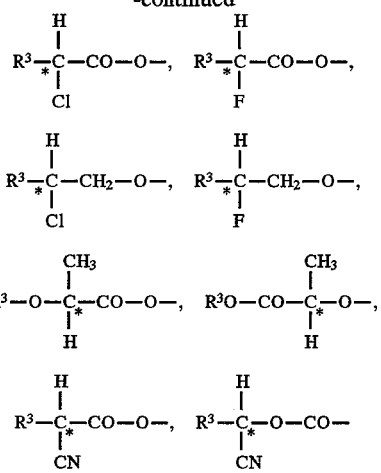

$A^1$, $A^2$, $A^3$ and $A^4$ are identical or different and are 1,4-phenylene, pyrimidine-2,5-diyl, where one or two hydrogen atoms may in each case be replaced by F, trans-1,4-cyclohexylene, in which one or two hydrogen atoms optionally are replaced by CN, 1,3,4-thiadiazole-2,5-diyl;

$M^1$, $M^2$, $M^3$ and $M^4$ are identical or different and are —O—, —CO—O—, —O—CO—, —O—CO—O—, —CH$_2$—O—, or —O—CH$_2$—;

$R^3$, $R^4$, $R^6$ and $R^7$ are identical or different and are H or straight-chain or branched alkyl having 1 to 16 carbon atoms, $M^5$ is —CH$_2$—O—, —CO—O—, —O—CH$_2$—, —O—CO— or a single bond;

k, l, m, n, o, p, q and r are zero or one, with the proviso that the sum k+m+p+r is less than 4 and greater than zero.

2. A 3-chloropyridine compound as claimed in claim 1, wherein the symbols in the formula (I) have the following meanings:

$R^1$ and $R^2$ are identical or different and are —H, or straight-chain or branched (with or without an asymmetric carbon atom) alkyl having 1 to 16 carbon atoms, optionally are one —CH$_2$—group to be replaced by,

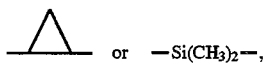

or are one of the following chiral groups

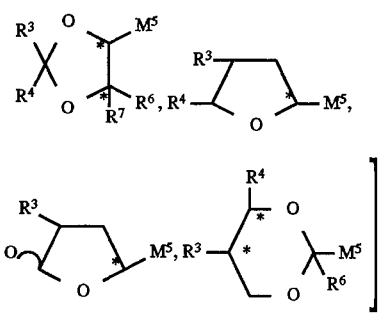

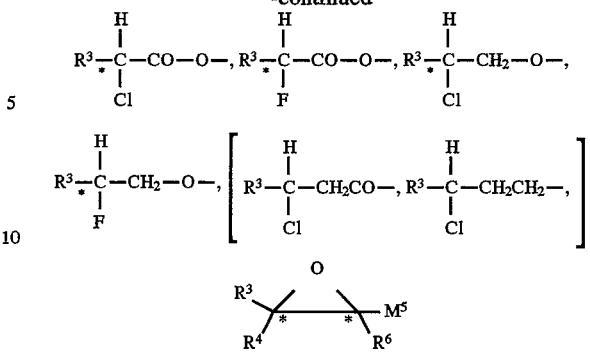

$A^1$, $A^2$, $A^3$ and $A^4$ are identical or different and are 1,4-phenylene, pyrimidine-2,5-diyl, where one or two hydrogen atoms may in each case be replaced by F, trans-1,4-cyclohexylene, 1,3,4-thia-diazole-2,5-diyl, or naphthalene-2,6-diyl;

$M^1$, $M^2$, $M^3$ and $M^4$ are identical or different and are —O—, —CO—O—, —O—CO—, —CH$_2$—O—, or —O—CH$_2$—;

$R^3$, $R^4$, $R^6$ and $R^7$ are identical or different and are H or straight-chain or branched alkyl having 1 to 10 carbon atoms;

$M^5$ is —CH$_2$—O—, —CO—O—, —O—CH$_2$—, —O—CO— or a single bond.

3. A 3-chloropyridine compound as claimed in claim 1, wherein the symbols in the formula (I) have the following meanings:

$R^1$ and $R^2$ are identical or different and are —H, or straight-chain or branched (with or without an asymmetric carbon atom) alkyl having 1 to 16 carbon atoms one

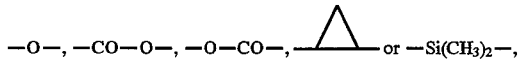

or are one of the following chiral groups:

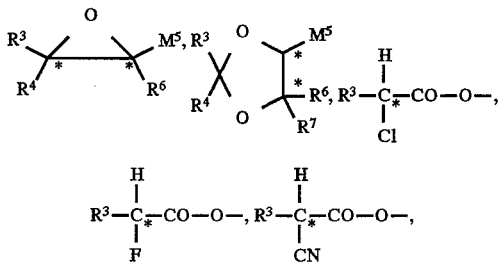

$A^1$, $A^2$, $A^3$ and $A^4$ are identical or different and are 1,4-phenylene, pyrimidine-2,5-diyl, in which one or two hydrogen atoms may in each case be replaced by F, trans-1,4-cyclohexylene, or naphthalene-2,6-diyl;

$M^1$, $M^2$, $M^3$ and $M^4$ are identical or different and are —O—, —CO—O—, —O—CO—, —O—CH$_2$—, or —CH$_2$—O—;

$R^3$, $R^4$, $R^6$ and $R^7$ are identical or different and are H or straight-chain or branched alkyl having 1 to 10 carbon atoms;

$M^5$ is —CH$_2$—O—, —CO—O—, —O—CH$_2$—, —O—CO— or a single bond.

4. A 3-chloropyridine compound as claimed in claim 1, wherein the symbols in the formula (I) have the following meanings:

$R^1$ and $R^2$ are identical or different and are H or alkyl having 1 to 16 carbon atoms, optionally wherein one —$CH_2$— group is replaced by —O—, —CO—O— or —O—CO—, or are the chiral group

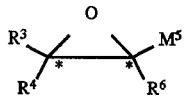

$A^1$, $A^2$, $A^3$ and $A^4$ are identical or different and are 1,4-phenylene, pyrimidine-2,5-diyl, in which one or two hydrogen atoms optionally are replaced by F, trans-1,4-cyclohexylene, or naphthalene-2,6-diyl;

$M^1$, $M^2$, $M^3$ and $M^4$ are identical or different and are —O—, —CO—O—, —O—CO—, —$OCH_2$—, or —$CH_2$—O—

$R^3$, $R^4$ and $R^6$ are identical or different and are H or straight-chain alkyl having 1 to 10 carbon atoms;

$M^5$ is —$CH_2$—O— or —CO—O—.

5. A 3-chloropyridine compound as claimed in claim 1, which is 3-chloro-5-octyl-2-(4-octyloxyphenyl)pyridine.

* * * * *

UNITED STATES PATENT AND TRADEMARK OFFICE
CERTIFICATE OF CORRECTION

PATENT NO. : 5,629,428
DATED : May 13, 1997
INVENTOR(S) : Schlosser et al.

It is certified that error appears in the above-indentified patent and that said Letters Patent is hereby corrected as shown below:

<u>Claim 1, line 6 of text</u>, please replace "it also being possible for" with -- optionally wherein --.

<u>Claim 1, line 7 of text</u>, please replace "to be" with -- is --.

Columns 27 and 28, the following formulas should read:

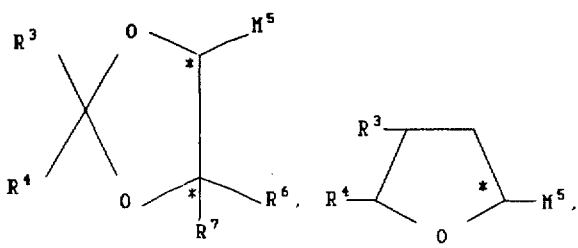

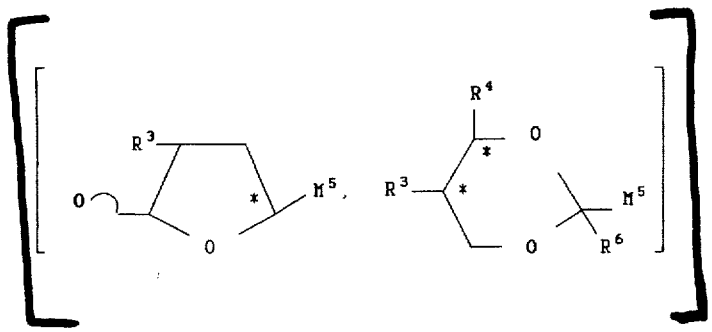

UNITED STATES PATENT AND TRADEMARK OFFICE
CERTIFICATE OF CORRECTION

PATENT NO. : 5,629,428  
DATED : May 13, 1997  
INVENTOR(S) : Schlosser et al.

Page 2 of 3

It is certified that error appears in the above-indentified patent and that said Letters Patent is hereby corrected as shown below:

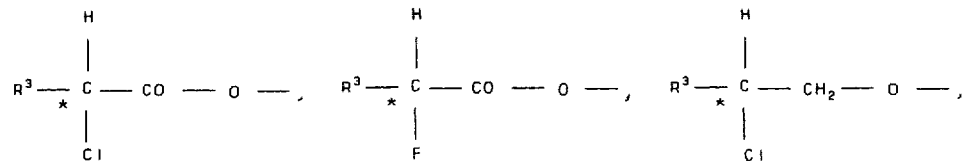

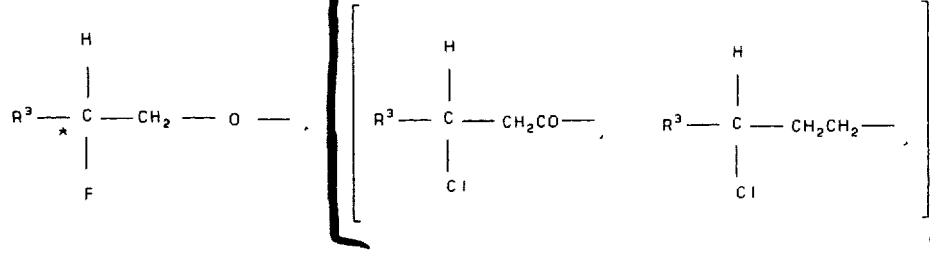

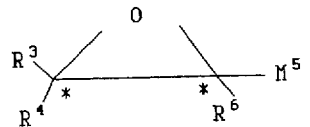

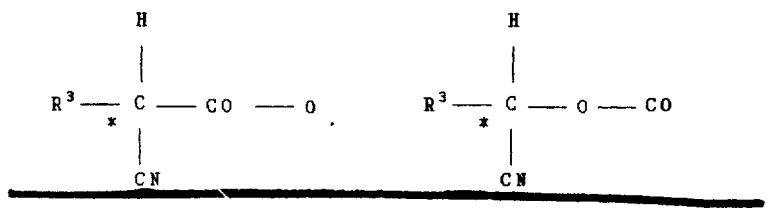

UNITED STATES PATENT AND TRADEMARK OFFICE
CERTIFICATE OF CORRECTION

PATENT NO. : 5,629,428
DATED : May 13, 1997
INVENTOR(S) : Schlosser et al.

It is certified that error appears in the above-indentified patent and that said Letters Patent is hereby corrected as shown below:

<u>Claim 3, line 6 of text</u>, after the word "atoms", please insert -- optionally wherein --.

<u>Claim 3, line 7 of text</u>, after the word "one", please insert -- -$CH_2$- group is replaced by --.

Signed and Sealed this

Twenty-eighth Day of October, 1997

*Attest:*

BRUCE LEHMAN

*Attesting Officer*  Commissioner of Patents and Trademarks